United States Patent [19]

Ishihara et al.

[11] Patent Number: 5,224,481
[45] Date of Patent: Jul. 6, 1993

[54] IMAGE DISPLAYING METHOD AND DEVICE FOR REALIZING SAME IN AN ULTRASONIC DIAGNOSTIC APPARATUS

[75] Inventors: Ken Ishihara, 1-5, Chigusa-1-chome, Takarazuka-shi; Jun Tanouchi, 1-141-119, Koyocho Naka-1-chome, Higashinada-ku, Kobe-shi; Takashi Sugiyama, Kashiwa; Shinji Kishimoto, Ibaraki, all of Japan

[73] Assignees: Ken Ishihara, Takarazuka; Jun Tanouchi, Kobe; Hitachi Medical Corporation, Tokyo, all of Japan

[21] Appl. No.: 755,746

[22] Filed: Sep. 6, 1991

[30] Foreign Application Priority Data

Sep. 7, 1990 [JP] Japan .................................. 2-235656

[51] Int. Cl.$^5$ .............................................. A61B 8/00
[52] U.S. Cl. .............................................. 128/660.07
[58] Field of Search .......... 128/660.01, 660.04-660.05, 128/660.07, 661.09-661.1, 654

[56] References Cited

U.S. PATENT DOCUMENTS 4,865,040 9/1989 Ogasawara ..................... 128/661.04

FOREIGN PATENT DOCUMENTS 189054 8/1987 Japan .

OTHER PUBLICATIONS

Heintzen, P. H. et al. "Digital Cardiovascular Radiology", in *Lecture Notes in Medical Informatics*, Dig. Image Proc. in Medicine, Proceedings Hamburg Oct. 5, 1981, pp. 1-14, 196-197.

*Primary Examiner*—Francis Jaworski
*Attorney, Agent, or Firm*—Antonelli, Terry, Stout & Kraus

[57] ABSTRACT

An image displaying method in an ultrasonic diagnostic apparatus obtains differential image data between first image data and second image data in image data sequentially obtained from an echo signal received by transmitting an ultrasonic wave to a body to be examined. A time difference between a point of time, where the first image data are measured, and another point of time, where the second image data are measured is determined. A synthesized image data capable of displaying simultaneously a differential image and the time difference by combining the differential image data and data representing the time difference is obtained and displayed.

12 Claims, 5 Drawing Sheets

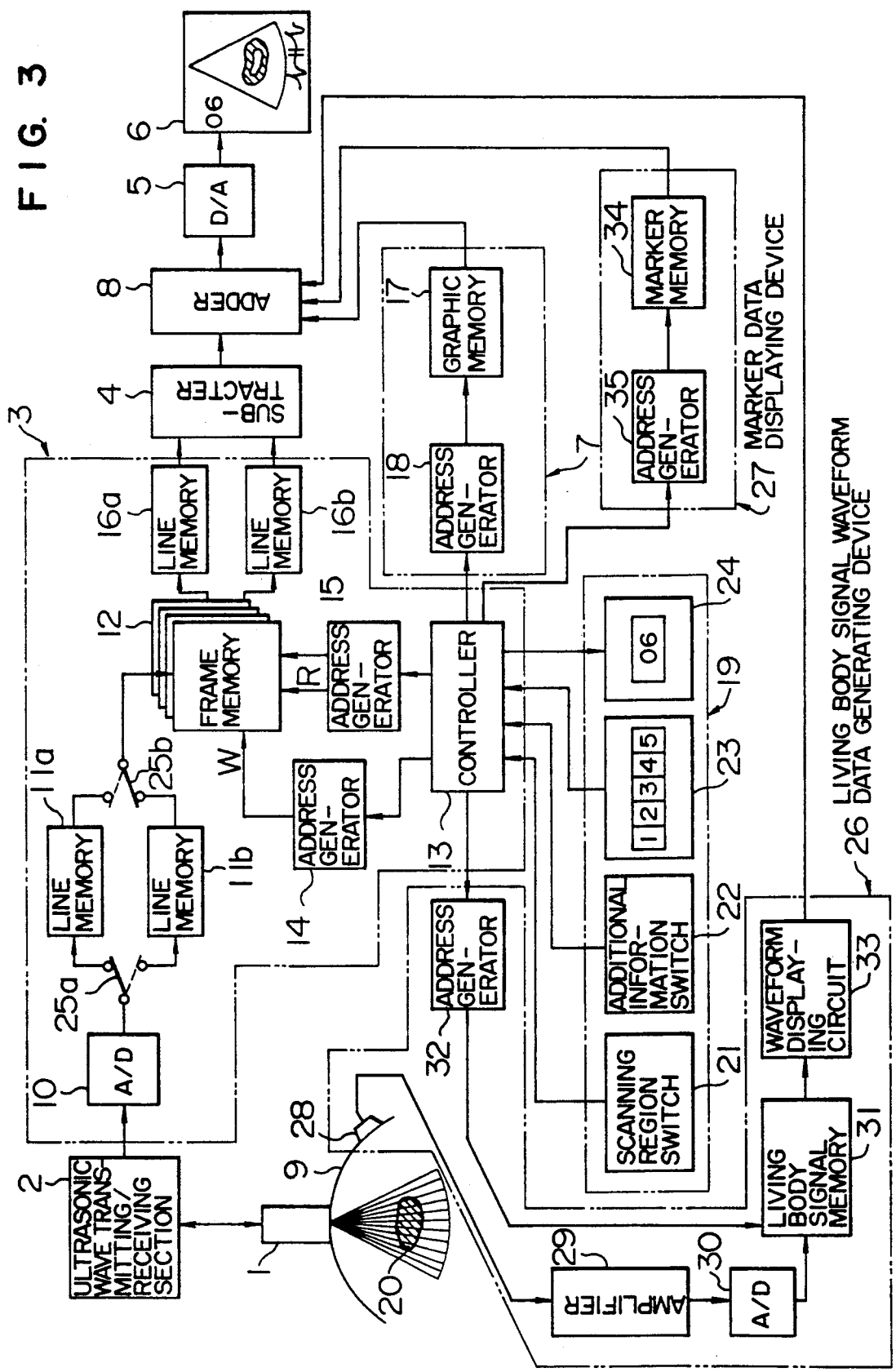

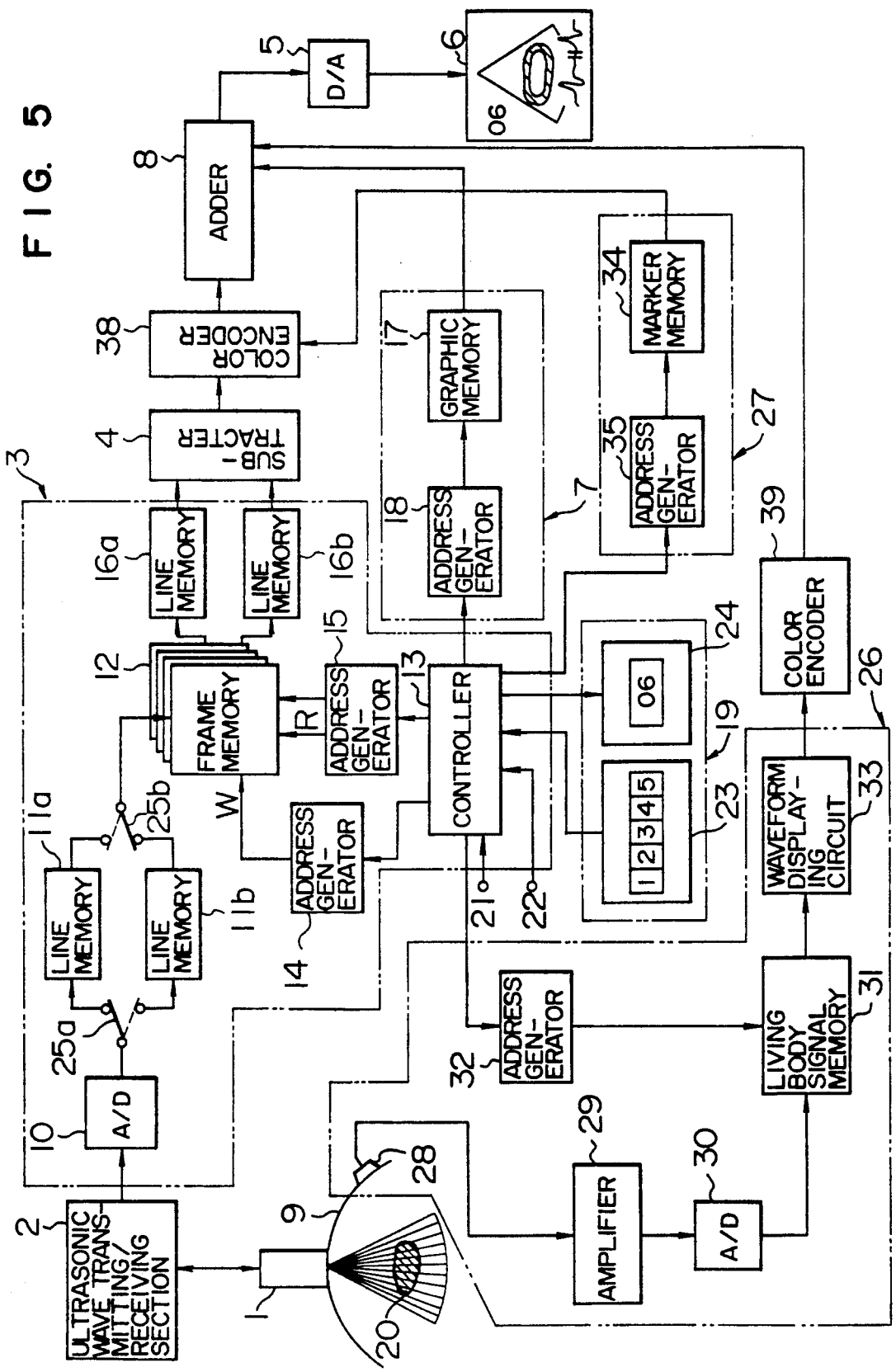

IMAGE DISPLAYING METHOD AND DEVICE FOR REALIZING SAME IN AN ULTRASONIC DIAGNOSTIC APPARATUS

BACKGROUND OF THE INVENTION

In a prior art ultrasonic diagnostic apparatus capable of depicting movement of a moving part within a body to be examined in the form of a differential image, as described in JP-A-62-189054, it has been proposed that an echo signal coming from an ultrasonic wave transmitting-receiving section is digitized and there are disposed a plurality of frame memories, in which data of tomographic images are stored sequentially, each of them storing data for one image, in a digital scan converter, which writes and reads the data in and from the frame memories contained therein and at the same time there is disposed on the output side of these frame memories a differential processor, in which the sequential data outputted from the different frame memories are inputted and which effects differential processing therebetween.

Further, as described in Report of 29th Meeting of the ME Society of Japan "3-H-3 Development of Digital Subtraction Echography (Medical Electronics and Living Body Technology, Vol. 28, p. 494, special print (1990) (in Japanese)), it has been proposed that an electrocardiogram of the body to be examined described above is displayed together with the differential image of the moving part in the body to be examined and at the same time a timing mark consisting of white and black parallel bars indicating the time difference between two images, for which a differential operation has been effected, is displayed.

However, in the first prior out example, although it is possible to extract only moving components for the moving part in the body to be examined to display them by using a differential image, no time difference between the two images, for which the differential operation has been effected to obtain the differential image, is displayed. Consequently the amount of displacement of the moving part described above can be detected, but the time required for the displacement cannot be obtained and therefore the speed of the displacement cannot be estimated. For this reason, diagnosis cannot be effected for the moving part in the body to be examined.

Further, in the second prior art example described above although the timing mark indicating the time difference between the two images, for which the differential operation has been effected, can be displayed on the electrocardiogram together with the differential image for the moving part in the body to be examined, this timing mark displays only indirectly the time difference corresponding to the differential operation by using the magnitude of the interval between the two parallel bars. Therefore it was impossible to display directly the time difference in the form of a numerical value. Consequently it was impossible to obtain directly the time required for the displacement of the moving part in the body to be examined and it happened that estimation of the speed of the displacement cannot be effected easily. For this reason, also in the second prior art example, diagnosis cannot be effected precisely for the moving part in the body to be examined.

SUMMARY OF THE INVENTION

The object of the present invention is to provide an ultrasonic diagnostic apparatus capable of displaying directly the amount of displacement of a moving part in a body to be examined and the time required for the displacement by displaying a differential image of the moving part described above and at the same time a numerical value representing the time difference between two images, for which the differential operation has been effected, in order to solve the problems as described above.

In order to achieve the above object, in an ultrasonic apparatus according to the present invention includes an ultrasonic wave transmitting/receiving device, which transmits and receives ultrasonic wave to and from a body to be examined; a tomographic scanning device for obtaining repeatedly with a predetermined period tomographic image data for the body to be examined including a moving texture by using a reflected echo signal coming from this ultrasonic wave transmitting/ receiving means; a device for effecting calculations between different sequential images obtained by this tomographic scanning means to obtain differential image data therefor; and an image displaying device for displaying these differential image data The apparatus of the invention also includes a device for displaying numerical data representing a time difference between two images, for which a differential operation is effected by the differential image data generating device described above and further a synthesizing device combining the differential image data described above with the numerical data from the numerical data displaying device in order to display simultaneously a differential image and a numerical value representing the time difference between two images, for which a differential operation has been effected.

Further, the apparatus according to the invention includes a device detecting a living body signal from the body to be examined and generating living signal waveform data and a device generating marker data indicating the time difference between two images, for which the differential image data generating device effects the differential operation, which are connected with the data synthesizing device described above so that the differential image, the numerical value representing the time difference between the two images, for which the differential operation has been effected, the living body signal waveform coming from the body to be examined, and the time difference marker utilizing this living body signal waveform as a time scale are displayed simultaneously on the image displaying device.

Furthermore, there may be disposed a control device, which controls the display of the differential image, the waveform of the body signal coming from the body to be examined and the time difference marker of the differential image described above in color in a same time phase and in a same color phase so that the color phase varies with the lapse of time.

Since the present invention is constructed as described above, it is possible not only to obtain directly the amount of displacement of the moving part in the body to be examined and the time required for the displacement but also to estimate easily the speed of the displacement only by looking at the content displayed on the screen of the image displaying means.

BRIEF DESCRIPTION OF THE DRAWINGS

FIG. 3 is a block diagram indicating a second embodiment of the present invention;

FIG. 5 is a block diagram indicating a third embodiment of the present invention.

DESCRIPTION OF THE PREFERRED EMBODIMENTS

Hereinbelow several embodiments of the present invention will be explained in detail, referring to the attached drawings.

Figure 1:
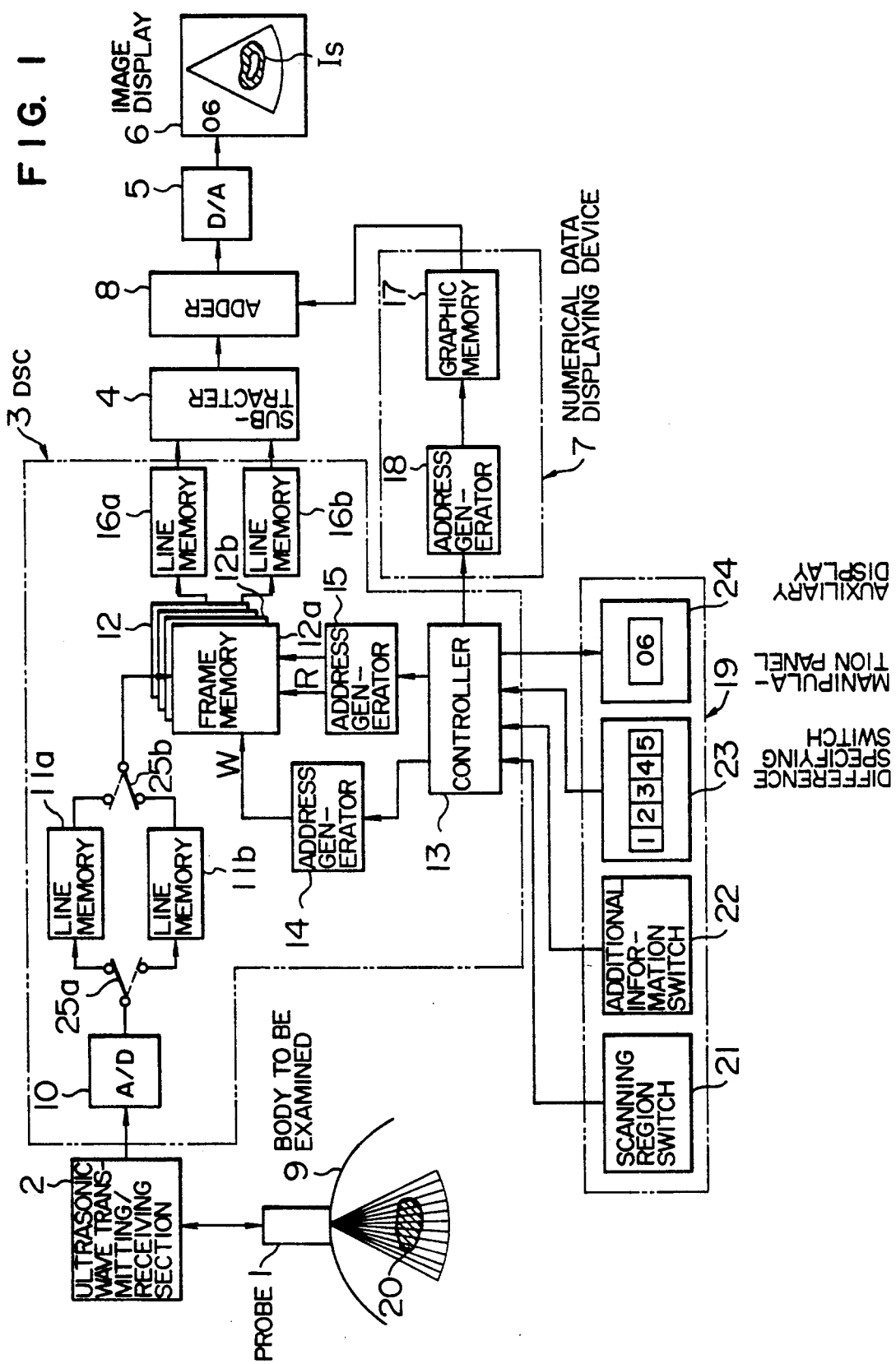
FIG. 1 is a block diagram indicating a first embodiment of the present invention.

FIG. 1 is a block diagram indicating an embodiment of the ultrasonic diagnostic apparatus according to the present invention. This ultrasonic diagnostic apparatus is used for obtaining a tomographic image for a part to be diagnosed in a body to be examined, utilizing ultrasonic wave and it comprises, as indicated in the figure, a probe 1, an ultrasonic wave transmitting/receiving section 2, a digital scan converter (hereinbelow abbreviated to DSC) 3, substracter 4, a D/A converter 5, and an image display 6. It is further provided with a numerical data displaying device 7 and an adder 8 serving as a data synthesizing device.

The probe 1 stated above scans the body 9 to be examined with a beam either mechanically or electronically and transmits and receives ultrasonic wave to and from the body 9 to be examined. A vibrator, which serves as a ultrasonic wave generating source and receives reflected echos, is incorporated therein, although it is omitted in the figure. The ultrasonic wave transmitting/receiving section 2 sends driving pulses to the probe 1 stated above and also processes received reflected echo signals. Although it is omitted in the figure, a wave transmitting pulser, a transmitted wave delaying circuit, a received wave amplifier, a received wave delaying circuit, an adder, etc. are incorporated in the ultra-sonic wave transmitting/ receiving section 2. These probe 1 and ultrasonic wave transmitting/receiving section 2 constitute the ultrasonic wave transmitting/receiving device. It scans the interior of the body 9 to be examined in a predetermined direction with an ultrasonic wave beam by means of the probe described above by a control signal coming from a controller 13 described later to obtain a tomographic image.

The DSC 3 takes-in tomographic image data on the interior of the body to be examined including a moving texture in synchronism with the reception of ultrasonic wave by using reflected echo signals outputted by the ultrasonic wave transmitting/receiving section 2 and at the same time it effects a scanning transformation by reading them with a timing synchronous to television. It comprises an A/D converter 10 converting reflected echo signals coming from the ultrasonic wave transmitting/receiving section 2 described above into digital signals; a plurality of line memories 11a, 11b; a plurality of frame memories 12 consisting of e.g. semiconductor memories, each of them being capable of storing 1 (one) frame of image data outputted by these line memories 11a, 11b; a controller 13 including e.g. a CPU, controlling the operation of these constituent elements, a first address generator 14 generating an address used at the time, where image data are written in the frame memories 12, by inputting a control signal from the controller 13; a second address generator 15 generating similarly an address used at the time, where the image data are read-out from the frame memories 12 described above; and two line memories 16a and 16b, in which the image data read-out from 2 (two) frame memories specified arbitrarily among the frame memories 12 described above are written for every television scanning line and also from which they are read-out.

The subtracter 4 serves as a device effecting calculations between sequential tomographical images obtained by the DSC 3 to generate differential image data therebetween, which performs subtractions between the tomographical data corresponding to the two images, while making pixels of different sets of image data correspond with each other between the image data outputted from one of the line memories 16a and the image data outputted from the other line memory 16b. Further the D/A converter 5 converts a signal synthesized from the differential image data outputted by the subtracter 4 stated above and an output of a graphic memory 17 into an analogue signal. Still further the image display 6, in which video signals from the D/A converter 5 are inputted, which are displayed thereon in the form of an image, and it consists of e.g. a television monitor. The D/A converter 5 and the image display 6 constitute an image displaying device.

Here, according to the present invention, the numerical data displaying device 7 is connected with the controller 13 in the DSC 3 described above and the adder 8 is connected after the subtracter 4 therewith. The numerical data displaying device 7 stated above displays numerical data representing the time difference between two images, for which the differential operation is effected by the subtracter 4. It consists of a graphic memory 17 storing numerical graphic data required for expressing the time difference and a third address generator 18, which generates an address used when the numerical graphic data representing the time difference stated above are read-out from the graphic memory 17 by inputting a control signal from the controller 13. Further the adder 8 adds the differential image data outputted by the subtracter 4 and the graphic data representing numerically the time difference outputted by the numerical data displaying device 7 to each other to synthesize an output signal.

In FIG. 1, a symbol 19 denotes a manipulation panel for the apparatus. On this manipulation panel 19 there are disposed a scanning region switch 21 specifying an operation region on the part to be diagnosed 20 in the body to be examined 9; an additional information switch 22 specifying additional information such as a body mark displyed or the image displayer 6; a difference specifying switch 23 specifying the interval between two images, for which a differential operation is effected on the image data by the subtracter 4, in the frame memories 12; and an auxiliary display 24 consisting of e.g. a liquid crystal display, displaying a numerical time difference corresponding to a value specified by this difference specifying switch 23.

Now the operation of the ultrasonic diagnostic apparatus according to the present invention thus constructed will be explained. At first the probe 1 indicated in FIG. 1 is brought into contact with a place corresponding to the part to be diagnosed 20 in the body 9 to be examined and ultrasonic wave is transmitted to the part to be diagnosed 20 stated above. At this time, the ultrasonic wave transmitted by the probe 1 is so transformed by a transmitted wave delaying circuit in the ultrasonic wave transmitting/receiving section 2 that a narrow beam is formed at the part to be diagnosed 20 described above. This transmitted wave beam is projected to the part to be diagnosed 20 and reflected thereby. A reflected echo thus produced is received by the probe 1 and taken-in through a received wave delaying circuit and an adder in the ultrasonic wave transmitting/receiving section 2, in which a received wave is formed. The ultrasonic wave transmitting/receiving direction from the probe 1 is changed successively with a predetermined period and the transmission/reception of the ultrasonic wave is repeated to scan the part to be diagnosed 20.

The reflected echo signal outputted from the ultrasonic wave transmitting/receiving section 2 is inputted in the A/D converter 10 in the DSC 3 and converted into a digital signal, which is sent to the succeeding line memories 11a and 11b. These line memories 11a and 11b are switched over by the switches 25a and 25b, every time the ultrasonic wave transmitting/receiving direction is changed by the controller 13, to control the write/read and the digital echo signal is sent to the succeeding frame memory 12 for every received beam inputted successively. At this time, for the frame memory 12 the writing address is specified by a control signal coming from the first address generator 14 and one set of sequential tomographic data is written in one of a plurality of frame memories 12 successively for every scanning with the ultrasonic wave.

Next, in order to read-out the tomographic data from the frame memories 12 to display the differential image, at first the difference specifying switch 23 on the manipulation panel 19 is manipulated to specify the time interval between two images, for which the differential operation is effected. For example, in the case where the differential operation is effected between two images adjacent to each other, a key "1" is pushed, while in the case where the differential operation is effected between one image and another next but one, another key "2" is pushed. Then, this specifying signal is sent to the second address generator 15 through the controller 13. For example two frame memories 12a and 12b adjacent to each other are specified, responding to the specifying signal described above and reading addresses are specified by a control signal outputted from the second address generator 15. The tomographic data are read-out from the frame memories with the timing of every television scanning line and at the same time they are written successively in two line memories 16a and 16b. Thereafter the tomographic data of the two images adjacent to each other are read-out from the two line memories 16a and 16b and inputted in the subtracter 4 to effect the differential operation between corresponding pixels of the two images. The differential image data obtained as the result between the two images are sent to the following adder 8.

At the same time, a specifying signal is inputted from the difference specifying switch 23 in the controller 13. Then, the controller 13 obtains a product of the interval of the emission of the ultrasonic wave determining the depth by the number of ultrasonic beams determining the size of the scanning region, i.e. a product of the time required for one frame of tomographic image by a numerical value specified by a key, responding to the specifying signal described above, and writes it in the graphic memory 17 through the address generator 18 in the form of numerical data. The read-out from the graphic memory 17 is effected through the address generator 18 by the controller 13 in synchronism with the read-out of the image data from the frame memory 12. In this way, numerical data corresponding to the time difference e.g. between two images adjacent to each other are read-out from the graphic memory 17 described above and sent to the adder 8.

Figure 2:
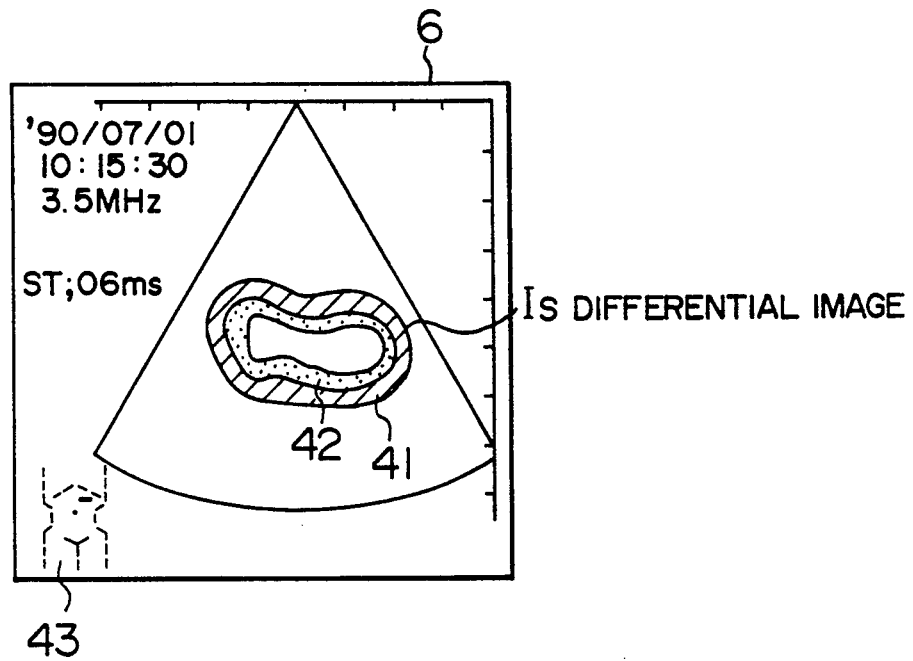
FIG. 2 is a scheme indicating an embodiment of a display screen according to the present invention.

In this way, the adder 8 adds the differential image data inputted from the subtracter 4 and the numerical data inputted from the numerical data displaying device 7 to each other to synthesize one set of image data displaying simultaneously the two kinds of data. Thereafter these synthesized image data are inputted in the D/A converter 5 to be converted into an analogue signal, which is inputted in the image display 6 and displayed there in the form of one image. At this time, a differential image Is for the part to be diagnosed 20 in the body 9 to be examined and the numerical value ST (e.g. 06 ms) representing the time difference between the two images, for which this differential operation has been effected, are displayed simultaneously on the image display 6, as indicated in FIG. 2. In the differential image Is a hatched portion 41 indicates an image of the moving part at a point of time $t_1$ and a half gray portion 42 indicates an image of the same moving part at another point of time $t_2$. 43 is a body mark showing the scanned part. In this way the operator can know the amount of displacement by the differential image Is and the time required for the displacement by the numerical value ST representing the time difference only by looking at one image on the image display 6.

At the same time, a signal specified by the difference specifying switch 23 described above, e.g. a signal corresponding to the key "1", is sent to the auxiliary display 24 on the manipulation panel 19. As the result, a numerical value representing the time difference obtained by the differential operation for the differential image Is, e.g. "06", is displayed on the auxiliary display 24. In this way it is possible for the operator to verify the numerical value representing the time difference between the two images obtained by the differential operation also on the manipulation panel 19. This auxiliary display 24 may not be always disposed.

FIG. 3 is a block diagram indicating a second embodiment of the present invention. In this embodiment, a living body signal waveform data generating device 26 and a marker data display device 27 are added to the embodiment indicated in FIG. 1, which are connected with the input side of the adder 8. Here the living body signal waveform data generating device 26 detects living body signals such as electrocardiographic waveform or phonocardiographic waveform, pulse wave, etc. of the body 9 to be examined to generate waveform data thereof. This device 26 comprises a living body signal detector 28 consisting of an electrocardiograph, a phonocardiograph, etc., which are attached on arms, legs, etc. of the body 9 to be examined; an amplifier 29, which amplifies living body signals consisting of weak electric signals detected by this living body signal detector 28; an A/D converter 30 converting analogue signals coming from this amplifier 29 into digital signals; a living body signal memory 31 storing living body signal data coming from this A/D converter 30; a fourth address generator 32 generating addresses used when the living body signal data are written in the living body signal memory 31 or when the living body signal data are read-out therefrom, by inputting a control signal from the controller 13; and a waveform displaying circuit 33, in which the living body signal data read-out from the living body signal memory 31 by an address specification by this fourth address generator 32 are inputted, which signal data are converted into graphic data having a waveform corresponding to the living body signal. The marker data displaying device 27 displays data consisting of two markers indicating the time difference between the two images, for which the differential operation is effected by the subtracter 4, as indicated by 34 in FIG. 4. The marker data displaying device 27 consists of a marker memory 34 storing graphic data representing two markers with different intervals generated by the controller 13 for indicating the time difference described above and a fifth address generator 35, in which a control signal is inputted from the control 13 and which generates the address used when the graphic data representing the two markers are written/read in/from the marker memory 34. The interval between the two markers corresponds to the time difference between the two images.

In this construction, since the storing of the tomographic image data in the frame memory 12 and the storing of the living body signal in the living body signal memory 31 can be easily frame-synchronized by the controller 13, the controller 13 produces the marker graphic data on the interval between the markers and the display position thereof, starting from the numerical value representing the time difference, and writes them in the marker memory 34. At the reading-out the address generator 35 is driven in synchronism with the address generator 15.

In this case, by an operation similar to that described above the differential image data coming from the subtracter 4 and the numerical data coming from the numerical data displaying device 7 are inputted in the adder 8. At the same time the living body signal waveform data coming from the living body signal waveform data generating device 26 and the marker data coming from the marker data displaying device 27 are inputted also in the adder 8 stated above. These data set are added together to synthesize one set of image data. Thereafter these synthesized image data are inputted in the D/A converter 5 and converted there into analogue signals. Then they are inputted in the image display 6 to be displayed in the form of one image. As the result, as shown in FIG. 4, in addition to the differential image Is which is the same as Is in FIG. 2 and numerical value ST representing the time difference between the two images, for which the differential operation has been effected, a living body signal waveform 36 such as electrocardiographic waveform, etc. of the body 9 to be examined at that time and the time difference marker 37 representing the time difference for the differential operation, using this living body signal waveform 36 serving as a time scale, are displayed simultaneously on the image display 6.

Figure 4:
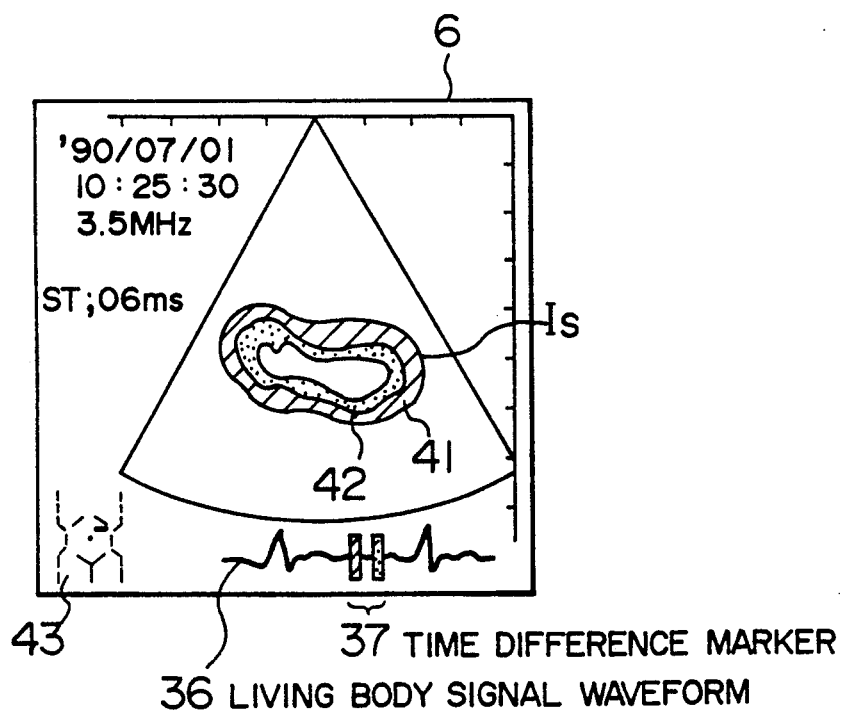
FIG. 4 is a scheme indicating another embodiment of the display screen according to the present invention.

In FIG. 4, the left bar of the time difference marker indicates a measuring time of the image 41 and the right bar indicates the measuring time of the image 42. At this time, the time difference marker 37 is displayed fixedly e.g. at a certain position on the screen of the image displayer 6 and the living body signal waveform 36 serving as the time scale is displayed, moving continuously e.g. to the left on the screen. In this way, the operator can know not only the amount of displacement by the differential image IS and the time required for the displacement by the numerical value ST representing the time difference, but also the position in the timing on the living body signal, for which the differential operation for the differential image Is indicated at present has been effected, depending on where the time difference marker 37 is located e.g. between an R wave and the succeeding R wave in an electrocardiographical waveform.

Although the present embodiment has been explained, supposing that the living body signal waveform 36 is moved (so-called scrawled) and the time difference marker 37 is fixed, it may be also conceivable that, on the contrary, the living body signal waveform 36 is fixed and the time difference marker 37 is moved. This method is useful particularly in the case where an ultrasonic image and a living body signal waveform are once stored in memory means and thereafter they are reproduced and displayed on the screen.

FIG. 5 is a block diagram indicating a third embodiment of the present invention. In the present embodiment, in addition to that indicated in FIG. 3, a first color encoder 38 is connected after the subtracter 4 therewith, in which the differential image data are inputted from the subtracter 4 and at the same time the marked data are inputted from the marker data displaying device 27, and further a second color encoder 39 is connected after the living body signal waveform data generating device 26 therewith, in which the living body signal waveform data are inputted. Here the first color encoder 38 and the second color encoder 39 control the display so that the color varies with the lapse of time, e.g. in rainbow colors, i.e. red, orange, yellow, green, blue, indigo and purple, with the lapse of time. In addition, the first color encoder 38 and the second color encoder 39 are made in accordance with each other in the time phase so that a same color phase is given to the image data, the living body signal data and the marker data.

In this case, the differential image data and the marker data are converted into color information by the first color encoder 38, while the living body signal waveform data are converted into color information by the second color encoder 39.

Figure 6:
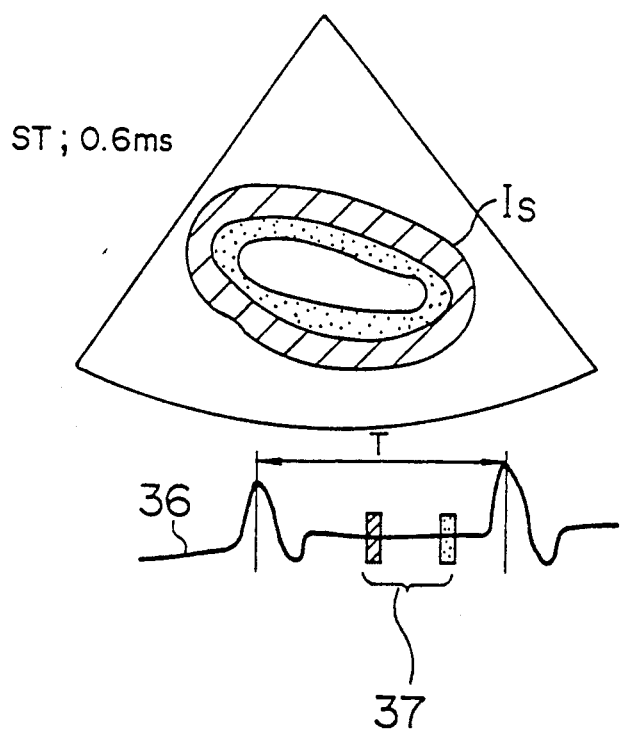
FIG. 6 is a scheme indicating still another embodiment of the display screen according to the present invention.

As indicated in FIG. 6, a certain period T on the living body signal waveform 36 is normalized in the form of a color display block, in which the color phase varies continuously with the lapse of time so that the time difference marker 37 and the differential image Is are displayed in a color phase corresponding to the lapse of time. In this way, the state of movement of the part to be diagnosed 20 in the body to be examined can be understood more easily by the variation in the color.

Further the second color encoder 39 capable of displaying the living body signal waveform in color may be omitted so that only the differential image Is and the time difference marker 37 are displayed in a display color, whose color phase varies, depending on the time difference.

We claim:

1. An image displaying method in an ultrasonic diagnostic apparatus comprising the steps of:
  (a) transmitting an ultrasonic wave to a body to be examined and receiving an echo signal coming from said body to be examined;
  (b) obtaining differential image data between first image data and second image data in image data sequentially obtained from said echo signal thus received;
  (c) obtaining a time difference data between a first measurement time, where said first image data are measured, and a second measurement time, where said second image data are measured;

(d) converting said time difference data to numeral data for display, said numeral data representing a time difference between said first and second measurement time;

(e) obtaining synthesized image data capable of displaying a differential image and said time difference by combining said differential image data and said numerical data; and (f) displaying said synthesized image data in the form of an image.

2. An image displaying method according to claim 1, wherein said step of obtaining a time difference comprises further:

a step of obtaining data representing living body information on said body to be examined; and a step of inputting said data representing living body information as a part of said synthesized image data.

3. An image displaying method according to claim 2, wherein said step of obtaining a time difference comprises further:

a step of obtaining data of markers representing said time difference; and a step of inputting said data of markers as a part of said synthesized image data.

4. An image displaying method according to claim 3, wherein said step of obtaining synthesized image data includes:

a step of synthesizing a set of data to display said living body information and said markers superposed on each other.

5. An image displaying method according to claim 2, wherein said step of obtaining data representing living body information includes:

a step of storing said living body information represented by a signal waveform.

6. An image displaying apparatus in an ultrasonic diagnostic apparatus comprising:

(1) means for transmitting an ultrasonic wave to a body to be examined and receiving an echo signal coming from said body to be examined;

(2) means for forming tomographic image data for said body to be examined from said echo signal thus received and storing them sequentially;

(3) means for obtaining differential image data between first image data and second image data in said image data;

(4) means for obtaining a time difference between a first measurement time, where said first image data are measured, and a second measurement time, where said second image data are measured;

(5) means for converting said time difference data to numerical data for display, said numeral data representing a time difference between said first and second measurement times;

(6) means for obtaining synthesized image data capable of displaying a differential image and said time difference by combining said differential image data and said numeral data; and (7) means for displaying said synthesized image data in the form of an image.

7. An image displaying device according to claim 6, wherein said means for obtaining a time difference comprises further:

means for storing data representing living body information on said body to be examined; and means for inputting said data representing living body information in said means for obtaining synthesized image data.

8. An image displaying device according to claim 7, wherein said means for storing data representing living body information includes:

a means for storing said living body information represented by a signal waveform.

9. An image displaying device according to claim 6, wherein said means for obtaining a time difference comprises further:

means for forming data of markers representing said time difference; and a means for inputting said data of markers in said means for obtaining synthesized image data.

10. An image displaying device according to claim 9, wherein said means for obtaining synthesized image data includes:

means for synthesizing a set of data to display said living body information and said markers superposed on each other.

11. An image displaying device according to claim 6, further comprising:

means for receiving a living body information signal which said body periodically generates;

means for converting said living body information signal to a waveform data for display;

means for assigning different colors for display to said waveform data according to a time phase;

means for assigning a first color to said first image data in said differential image data and a second color to said second image data in said differential image data, said first color being the same as the color assigned to said waveform at said first measurement time, said second color being the same as the color assigned to said waveform at said second measurement time; and means for displaying said differential image data with said first and second colors and said waveform data with said different colors on a display screen.

12. An image displaying method according to claim 1, further comprising the steps of:

receiving a living body information signal which said body periodically generates, when said echo signal is received in said step (a);

converting said living body information signal to a waveform data for display;

assigning different colors for display to said waveform data according to a time phase;

assigning a first color to said first image data in said differential image data and a second color to said second image data in said differential image data, said first color being the same as the color assigned to said waveform at said first measurement time, said second color being the same as the color assigned to said waveform at said second measurement time; and displaying said differential image data with said first and second colors and said waveform data with said different colors on a display screen.

* * * * *